US008945825B2

(12) United States Patent
Dekevic et al.

(10) Patent No.: US 8,945,825 B2
(45) Date of Patent: Feb. 3, 2015

(54) HOMOGENEOUS ACTIVITY TEST FOR DETERMINING ENZYMATIC REACTIONS

(75) Inventors: Katharina Dekevic, Stuttgart-Rot (DE); Herbert Schwarz, Lohra (DE); Frank Vitzthum, Lahntal (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 278 days.

(21) Appl. No.: 13/153,693

(22) Filed: Jun. 6, 2011

(65) Prior Publication Data
US 2011/0306066 A1 Dec. 15, 2011

(30) Foreign Application Priority Data

Jun. 10, 2010 (EP) ..................... 10005971

(51) Int. Cl.
*C12Q 1/00* (2006.01)
*G01N 33/573* (2006.01)
*G01N 33/86* (2006.01)
*G01N 33/50* (2006.01)
*G01N 33/58* (2006.01)
*G01N 33/542* (2006.01)
*G01N 21/64* (2006.01)

(52) U.S. Cl.
CPC .............. *G01N 33/573* (2013.01); *G01N 33/86* (2013.01); *G01N 33/5041* (2013.01); *G01N 33/58* (2013.01); *G01N 33/542* (2013.01); *G01N 2500/00* (2013.01); *G01N 2021/6432* (2013.01); *G01N 2021/6441* (2013.01); *G01N 2333/745* (2013.01); *G01N 2333/95* (2013.01); *G01N 2333/96433* (2013.01); *G01N 2500/02* (2013.01)
USPC .................................. 435/4; 435/183; 435/13

(58) Field of Classification Search
CPC .......... G01N 2500/00; G01N 33/5008; G01N 2021/6441; G01N 33/542; G01N 33/86; C12N 9/644; C12N 9/6437; C12N 9/6429; C12N 9/6443; C12N 9/6451; C12N 9/6424; C12N 9/647; C12Q 1/37; C12Y 304/21022; C12Y 304/21021
USPC ............. 435/4, 7.71, 7.72, 13, 176, 177, 181, 435/184, 183; 436/537
See application file for complete search history.

(56) References Cited

U.S. PATENT DOCUMENTS 3,996,345 A 12/1976 Ullman et al. ....... G01N 33/542
(Continued)

FOREIGN PATENT DOCUMENTS

AU 642733 B2 10/1993 ............. A61K 31/00
EP 0420332 A2 4/1991 ............... C12Q 1/56
(Continued)

OTHER PUBLICATIONS

Kannemeier, C. et al., Factor VII and Single-Chain Plasminogen Activator-Activating Protease, Eur. J. Biochem 2001, 268, 2789-2796; Magazine; (8 pages), Feb. 2001.
(Continued)

*Primary Examiner* — Melanie Y Brown
*Assistant Examiner* — Erik B Crawford
(74) *Attorney, Agent, or Firm* — King & Spalding L.L.P.

(57) ABSTRACT

A homogeneous method for determining the enzymatic activity of an analyte in a sample permits simultaneous determination of the amount of enzyme in the same reaction mixture and determination of enzyme activators or inhibitors.

14 Claims, 2 Drawing Sheets

(56) References Cited

U.S. PATENT DOCUMENTS

| | | | |
|---|---|---|---|
| 5,478,810 A | 12/1995 | Stuber et al. | ............ C07K 14/75 |
| 2002/0142316 A1 | 10/2002 | Roemisch et al. | ..... G01N 33/53 |
| 2003/0077271 A1* | 4/2003 | Kannemeier et al. | ...... 424/94.64 |
| 2003/0215447 A1 | 11/2003 | Roemisch et al. | ... G01N 33/573 |
| 2004/0005582 A1* | 1/2004 | Shipwash | ......................... 435/6 |
| 2009/0042193 A1* | 2/2009 | Heroux et al. | .................... 435/6 |

FOREIGN PATENT DOCUMENTS

| | | | |
|---|---|---|---|
| EP | 0456152 A2 | 11/1991 | ............. A61K 31/00 |
| EP | 0515194 A2 | 11/1992 | ........... C07D 265/30 |
| EP | 1334983 A2 | 8/2003 | ........... A61K 39/395 |
| EP | 1650305 A1 | 4/2006 | ............ A61K 38/48 |
| WO | 95/06877 A1 | 3/1995 | ........... C07D 311/20 |

OTHER PUBLICATIONS

Baker, K. et al., Chemical Complementation: A Reaction-Independent Genetic Assay for Enzyme Catalysis, PNAS 2002, vol. 99, No. 26, 16537-16542; Magazine; (6 pages), Oct. 23, 2002.

Udenfriend, S. et al., Scintillation Proximity Radioimmunoassay Utilizing 125-I-labelled ligands, Proc. Natl. Acad. Sci. USA 1985,82,8672-8676; Magazine; (6 pages), Aug. 6, 1985.

Eglen, R.M., Enzyme Fragment Complementation; A Flexible High Throughout Screening Assay Technology, Assay and Drug Development Technologies 2002, vol. 1, No. 1-1, 2002, 97-104; Magazine; 2002 (8 pages).

Charter, N.W. et al., A Generic Homogenous Method for Measuring Kinase and Inhibitor Activity via Adenosine 5'-Diphosphate Accumulation. Journal of Biomolecular Screening 2006, 11(4), 390-399; Magazine; 2006 (10 pages).

* cited by examiner

HOMOGENEOUS ACTIVITY TEST FOR DETERMINING ENZYMATIC REACTIONS

CROSS-REFERENCE TO RELATED APPLICATIONS

This application claims priority to EP Patent Application No. 10005971 filed Jun. 10, 2010, the contents of which is incorporated herein by reference in its entirety.

TECHNICAL FIELD

The present invention is in the area of in-vitro diagnostics and relates to a homogeneous method of determining enzymatically catalyzed reactions in a sample. With the determination, according to various embodiments, of enzymatically catalyzed chemical reactions it is possible to determine the activity state of enzymes or the presence of substances that have an effect on the activity state.

BACKGROUND

A chemical reaction is a process in which substances are transformed. One or more reaction products form from one or more starting substances (educts or reactants). The chemical or physical properties of the product are different from those of the educt.

In an enzymatically catalyzed reaction, an enzyme participates in the initiation, acceleration or control of the chemical reaction.

Many diagnostically relevant parameters are enzymes, reactants, reaction products or modulators of enzyme activity. An activity modulator is to be understood as a substance that is able to influence the activity of an enzyme, as inhibitor, activator, agonist, antagonist or cofactor.

An example of a diagnostically relevant enzyme is thrombin, a blood clotting factor in the serine protease group, determination of the activity of which in a patient's plasma sample can provide information about the status of the patient's blood coagulation. Another example is the blood clotting factor VII activating protease (FSAP), determination of the activity of which can for example provide information about a patient's risk of developing a thrombosis.

The activity of an enzyme is usually determined from the reaction of a more or less specific substrate. The known methods are divided into homogeneous methods (without separation steps) and heterogeneous methods (with one or more separation steps).

In heterogeneous methods, the substance to be detected is enriched. That is, the sample being investigated is submitted to a process by which the concentration of other constituents of the sample is reduced relative to the substance to be detected or they are removed completely. Affinity techniques, for example, are used for this.

In contrast, in homogeneous methods the samples are investigated in the assay directly. Separation processes, for example washing steps, are not used.

Examples of homogeneous methods of determining the activity of an enzyme are e.g. thrombin activity assays, such as the ETP assay, as described in EP-A2-0420332. The thrombin in a plasma sample is activated, and a chromogenic peptide substrate is mixed with the sample, and its specific cleavage by thrombin is measured photometrically. This homogeneous assay format is not, however, suitable for determining the activity of enzymes with low substrate specificity, as the lack of substrate specificity means that the substrate can also be converted by other enzymes from the sample. Homogeneous methods are also unsuitable for the determination of enzymes for which only substrates with inadequate analytical sensitivity are available. Furthermore, this homogeneous assay format as a rule is also unsuitable for determining the activity of enzymes with low volume activity.

The volume activity describes the catalytic activity of an enzyme per unit volume. The catalytic activity is defined by the amount of substrate that is reacted in unit time, or the amount of product that is formed in unit time. The volume activity is often stated in $\mu$mol (substrate degradation or product formation) per minute and per liter, i.e. $\mu$mol/min*L. For $\mu$mol/min, usually the term unit (U) or catalytic unit (kU) is used. According to the International System of Units (SI) the unit katal (kat) should be used, i.e. mol/sec.

Along with the volume activity of an enzyme in a sample, in particular the specific activity of an enzyme describes its activity state. The specific activity is found from the ratio of the catalytic activity of an enzyme to the amount of the enzyme present, i.e. $\mu$mol/min*g (U/g). The specific activity can for example provide information about the degree of activation, the degree of degradation or the inhibition or activation of an enzyme.

If a sample to be investigated contains other enzymes, which also transform the substrate used, which may be the case in particular in complex samples such as samples of body fluids, specific determination of the desired enzyme activity cannot be carried out directly in the sample without a suitable highly specific substrate.

In the prior art, this problem can be solved for example by determining, instead of the enzyme activity, the enzyme concentration or antigen concentration by means of a specific assay, for example by means of an immunoassay. The antigen concentration is correlated with the expected enzyme activity. Estimating the enzyme activity from the enzyme concentration is unsuitable if the activity state of the enzyme is for example influenced by activity modulators. Therefore the activity of an enzyme or its activity state cannot always be determined with certainty.

Furthermore, in the prior art the problem is also usually solved by using heterogeneous assay systems. In this case the enzyme to be detected is separated from the other constituents of the sample, before the enzyme activity is determined. Separation is usually effected by contacting the sample with a solid phase that has a specific binding affinity for the enzyme to be detected, and subsequent separation of the solid phase.

The disadvantage of these heterogeneous methods is that they include at least one separation step, and perhaps even additional washing steps. These additional steps make automation more difficult and lengthen the processing time. The processing time is also longer because the sample may be incubated with the solid phase for a certain length of time, to enable the enzyme to be detected to bind to the solid phase. Another disadvantage is that the incubation, separation and washing of the solid phase can have an effect on the activity of the enzyme to be detected. For example, conformational changes or degradation of the enzyme can lead to changes in activity. Another disadvantage of the heterogeneous methods is that other constituents of the sample are removed or at least their concentrations are reduced, so that binding partners, cofactors, activators or inhibitors that are intrinsic to the sample, and which influence the activity of the enzyme to be detected, are also removed, so that the enzyme activity or possible binding partners of the enzyme cannot be determined in the physiological context of the sample matrix.

SUMMARY

According to various embodiments, a homogeneous method can be provided, which makes possible the specific determination of the activity of an enzyme even in the presence of disturbing enzymes, which also transform the substrate used. Moreover, according to various embodiments, the activity state of an enzyme can be determined, i.e. apart from the volume activity, also obtain an indication of the enzyme concentration and thus the specific activity or the presence of activity modulators. In particular, determination, preferably quantitative determination, of the specific activity or of activity modulators can be made possible according to various embodiments. Furthermore, according to various embodiments it may be possible to determine the activity of an enzyme that is present in low volume activity.

According to an embodiment, a method of determining the activity of an enzyme in a sample, may comprise the following steps:
 a) preparation and incubation of a reaction mixture containing
  i) the sample,
  ii) at least one substrate, which can be bound and converted by the enzyme to be determined,
  iii) a first and a second component of a signal-forming system, which interact so that a detectable signal is produced when the first and the second components of the signal-forming system are brought spatially close to one another and wherein the substrate is associated with the first component of the signal-forming system or becomes associated during incubation and wherein the enzyme to be determined becomes associated with the second component of the signal-forming system during incubation; and
 b) measurement of the signal, which is correlated with the enzyme activity in the sample.

According to a further embodiment, the substrate may have a first binding partner A of a first binding pair A/B and wherein the first component of the signal-forming system has the second binding partner B of the first binding pair A/B and wherein the substrate is bound by binding of the binding partners A and B to the first component of the signal-forming system or becomes bound during incubation. According to a further embodiment, the binding partners A and B can be selected so that they form a binding pair A/B from the group comprising FLAG-tag/anti-FLAG-tag antibodies, HIS-tag/anti-HIS-tag antibodies, fluorescein/anti-fluorescein antibodies, biotin/avidin and biotin/streptavidin. According to a further embodiment, the enzyme to be determined may have a first binding partner X of a second binding pair X/Y and wherein the second binding partner Y of the second binding pair X/Y is associated with the second component of the signal-forming system and wherein the enzyme is bound by binding of the binding partners X and Y during incubation to the second component of the signal-forming system. According to a further embodiment, the binding partners X and Y can be selected so that X is an enzyme-specific structural or sequence epitope and Y is an antibody or antibody fragment with specificity for the enzyme-specific structural or sequence epitope. According to a further embodiment, the first component of the signal-forming system can be associated with a first particulate solid phase and the second component of the signal-forming system is associated with a second particulate solid phase. According to a further embodiment, the first component of the signal-forming system can be a chemiluminescent agent and the second component of the signal-forming system is a photosensitizer, or vice versa. According to a further embodiment, the method can be used for determining the activity of an enzyme from the hydrolase group, in particular peptidases such as for example serine proteases, glycosidases, glycosylases and nucleases.

According to a further embodiment, the method can be used for determining the activity of an enzyme from the protease group, in particular serine proteases. According to a further embodiment, the method can be used for determining the activity of a proteolytic clotting factor from the group comprising factor II, factor VII, factor IX, factor X, factor XI, factor XII and protein C, wherein additionally an agent for direct or indirect activation of the proteolytic clotting factor in the sample is added to the reaction mixture. According to a further embodiment, an agent from the group comprising thromboplastin, factor IIa, factor VIIa, factor IXa, factor Xa, factor XIa, factor XIIa, activated protein C, snake venoms, negatively charged phospholipids, calcium ions, tissue factor, silica, kaolin, ellagic acid, Celite can be used for the direct or indirect activation of the proteolytic clotting factor. According to a further embodiment, the method can be used for determining the activity of factor VII activating protease. According to a further embodiment, the amount of the enzyme can be determined simultaneously, in the same reaction mixture, additionally comprising the following steps:
 a) addition of a third component of the signal-forming system to the reaction mixture,
  i) which becomes associated with the enzyme to be determined during incubation and
  ii) which interacts with the second component of the signal-forming system so that a second detectable signal is produced, when the third and the second component of the signal-forming system are brought spatially close to one another, wherein the second signal is different from the signal that results from the interaction of the first and second component of the signal-forming system, and
 b) measurement of the second signal, which is correlated with the amount of enzyme in the sample.

According to a further embodiment, the enzyme to be determined may have a first binding partner C of a third binding pair C/D and wherein the second binding partner D of the third binding pair C/D is associated with the third component of the signal-forming system and wherein the enzyme is bound to the third component of the signal-forming system by binding of the binding partners C and D during incubation. According to a further embodiment, the first component of the signal-forming system can be associated with a first particulate solid phase and the second component of the signal-forming system is associated with a second particulate solid phase and the third component of the signal-forming system is associated with a third particulate solid phase. According to a further embodiment, the first component of the signal-forming system can be a first chemiluminescent agent and the second component of the signal-forming system is a photosensitizer and the third component is a second chemiluminescent agent, and wherein the first and second chemiluminescent agents have emission spectra different from one another. According to a further embodiment, the first component of the signal-forming system can be a first photosensitizer and the second component of the signal-forming system is a chemiluminescent agent and the third component is a second photosensitizer and wherein the first and second photosensitizers are excitable by light of different wavelength.

According to another embodiment, a method of quantitative determination of an enzyme modulator in a sample, may comprise the following steps:
 a) preparation and incubation of a reaction mixture containing
  (i) the sample,
  (ii) a defined amount of an enzyme, whose activity can be influenced directly or indirectly by the modulator of enzyme activity to be determined, and where the enzyme is contained in a separate reagent, which is added to the reaction mixture, (iii) a substrate, which can be bound and modified by the added enzyme, (iv) and a first and a second component of a signal-forming system, where the first component of the signal-forming system is or will become associated with the substrate and where the second component of the signal-forming system is associated with the added enzyme, where the signal-forming system is such that a detectable signal is only produced if the first and the second component of the signal-forming system are brought spatially close to one another by binding of the enzyme to be determined to the substrate, and b) measurement of the signal, which is correlated with the activity of the enzyme modulator in the sample.

According to a further embodiment, the above method can be used for determining an inhibitor of a blood clotting factor, wherein a defined amount of an activated blood clotting factor is added. According to a further embodiment, the above method can be used for an inhibitor of a blood clotting factor from the group comprising heparin, argatroban, melagatran, ximelagatran, bivalirudin, dabigatran, rivaroxaban and hirudin.

DETAILED DESCRIPTION

Figure 1:
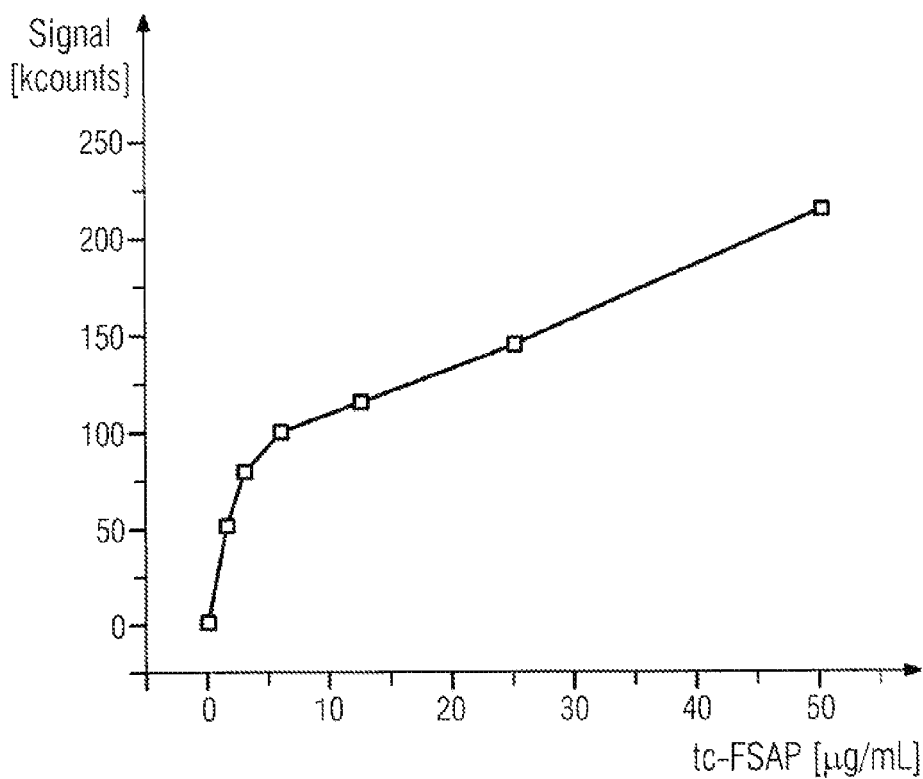
FIG. 1 shows the dependence of the LOCI signal on the enzyme activity or concentration.

This problem is solved in that a substrate and a first and a second component of a signal-forming system are added to the sample being investigated, wherein the first component of the signal-forming system is or will become associated with the substrate and wherein the second component of the signal-forming system will become associated with the enzyme to be determined. The signal-forming system is such that a detectable signal is only produced if the first and the second component of the signal-forming system are brought spatially close to one another by binding of the enzyme to be determined to the substrate. The binding of other possible disturbing enzymes to the substrate does not lead to a signal being generated, because exclusively the enzyme to be detected is associated with the second component of the signal-forming system. The resultant signal provides information about the activity of the enzyme in the sample.

The various embodiments relate to a method of determining the activity of an enzyme in a sample.

The term "enzyme" means, in the sense of the present invention, any substance that is able to catalyze a reaction, without being consumed in the process. The term "enzyme" includes proteins and nucleic acids, for instance catalytically active RNA molecules, so-called ribozymes. Depending on function, an enzyme is essentially assigned to one of the following classes: oxidoreductases, transferases, hydrolases, lyases, isomerases or ligases. In particular the term "enzyme" includes the blood coagulation factors factor II, factor VII, factor IX, factor X, factor XI, factor XII, factor XIII, protein C, factor VII activating protease (FSAP), prekallikrein, plasminogen, tissue plasminogen activator (tPA), prourokinase.

The term "sample" means, in the sense of the present invention, the material that is presumed to contain the enzyme to be detected. The term "sample" comprises biological fluids or tissues, in particular from humans and animals, such as blood, plasma, serum and other body fluids, secretions or extracts. Optionally, a sample has to be pretreated, to make the enzyme accessible by the detection method or to remove disturbing constituents from the sample. This pretreatment of a sample may include the separation and/or lysis of cells, the precipitation, hydrolysis or denaturation of constituents of the sample, for instance proteins, the centrifugation of samples, treating the sample with organic solvents, for instance alcohols, in particular methanol; treating the sample with detergents. Often the sample is transferred to another, generally aqueous, medium, which if at all possible should not interfere with the detection method.

The method according to various embodiments comprises the provision of a reaction mixture containing the sample, at least one substrate, which can be bound by the enzyme to be determined and converted to at least one product, and a first and a second component of a signal-forming system, which interact so that a detectable signal is produced when the first and the second component of the signal-forming system are brought spatially close to one another. The substrate is or will become associated with the first component of the signal-forming system; the enzyme to be determined is associated with the second component of the signal-forming system. As a result of complexation between enzyme and substrate, the components of the signal-forming system are brought spatially close to one another, so that a detectable signal is produced, which is correlated with the activity of the enzyme in the sample.

The term "substrate" means, in the sense of the present invention, a substance that is bound by the enzyme and is converted to at least one reaction product. Preferred substrates, e.g. for detecting peptidases, which cleave peptide bonds hydrolytically, consist of proteins, peptides or comprise at least one peptide moiety.

The term "signal-forming system" means, in the sense of the present invention, a system that comprises at least a first and a second component, which interact so that a detectable signal is produced, when they are brought spatially close to one another and can thus interact with one another. Interaction between the components means in particular a transfer of energy—that is, the direct transfer of energy between the components, e.g. by radiation of light or electrons and via reactive chemical molecules, for instance short-lived singlet oxygen. The energy transfer can take place from one component to another, but a cascade of different substances, over which energy transfer occurs, is also possible. For example, the components can be a pair comprising an energy donor and an energy acceptor, for example photosensitizer and chemiluminescent agent (EP-A2-0515194, LOCI® technology) or photosensitizer and fluorophore (WO 95/06877) or radioactive iodine-125 and fluorophore (Udenfriend et al. (1985) Proc. Natl. Acad. Sci. 82:8672-8676) or fluorophore and fluorescence quencher (U.S. Pat. No. 3,996,345).

The first component and/or the second component of the signal-forming system can be associated covalently or by specific interaction with a particulate solid phase or can be intercalated in the latter. The term "particulate solid phase" means suspensible particles, for instance metal sols, silica particles, magnetic particles or especially preferably latex particles. Particles with a diameter of 0.01-10 micrometer are preferred, and particles with a diameter of 0.1-1 micrometer are especially preferred.

In one embodiment of the method the substrate has a first binding partner A of a first binding pair A/B, and the first component of the signal-forming system has the second binding partner B of the binding pair A/B, so that the substrate can be associated with the first component of the signal-forming system. The binding of the substrate to the first component of the signal-forming system can either take place during incubation of the reaction mixture, i.e. in the presence of the sample and the second component of the signal-forming system, or the substrate and the first signal-forming component are incubated separately before they are added to the reaction mixture and the complex of substrate and first component of the signal-forming system is added to the reaction mixture.

The binding partners A and B are two different molecules, which recognize and bind one another specifically. Examples of specific recognition and binding are antibody-antigen interactions, enzyme-substrate interactions, polynucleotide interactions etc.

Suitable binding pairs A/B are mainly antigen/antibody combinations, where the binding partner A is an antigenic epitope of the substrate. The antigenic epitope can be a natural sequence epitope or structural epitope of a natural protein or protein fragment. The antigenic epitope can also be a heterologous sequence epitope or structural epitope of a modified substrate. Examples of heterologous sequence epitopes or structural epitopes are FLAG, or HIS or fluorescein tags, which are used in particular for labeling peptides or proteins. Other suitable binding pairs A/B are complementary polynucleotides A and B. The binding partner B associated with the first component of the signal-forming system is to be selected so that the substrate can be bound specifically. Preferably the binding partner B consists of an antibody or an antigen-binding fragment thereof. Especially preferred binding pairs A/B are FLAG-tag/anti-FLAG-tag antibodies, HIS-tag/anti-HIS-tag antibodies, fluorescein/anti-fluorescein antibodies, biotin/avidin and biotin/streptavidin.

In another embodiment of the method the enzyme to be determined has a first binding partner X of a second binding pair X/Y, and the second component of the signal-forming system is associated with the second binding partner Y of the binding pair X/Y, so that the enzyme to be determined is bound, by binding of the binding partners X and Y during incubation of the reaction mixture, to the second component of the signal-forming system.

The binding partners X and Y are two different molecules, which recognize and bind one another specifically. X is an enzyme-specific structural or sequence epitope, and Y is—depending on the nature of the enzyme to be detected—an antibody or antibody fragment or a polynucleotide with specificity for the enzyme-specific structural or sequence epitope.

A further embodiment relates to a method of determining the activity of a proteolytic clotting factor from the group comprising factor II, factor VII, factor IX, factor X, factor XI, factor XII and protein C, wherein an agent for direct or indirect activation of the proteolytic clotting factor in the sample is additionally added to the reaction mixture.

For direct or indirect activation of the proteolytic clotting factor in the sample, the sample is usually mixed with an agent that brings about direct or indirect activation of the proteolytic clotting factor. "Direct activation" means that an agent is used which directly activates the proteolytic clotting factor to be determined, independently of the presence of other clotting factors. "Indirect activation" means that an agent is used that activates one or more blood coagulation factors of the blood coagulation cascade, which in their turn activate the proteolytic clotting factor to be investigated. The type of agent depends on which clotting factor is to be determined, whether the activity of the clotting factor alone is to be determined or whether the functionality of the blood coagulation cascade or a partial region of the blood coagulation cascade (extrinsic or intrinsic pathway) is to be determined by means of a clotting factor. Substances and specific mixtures of various substances, which permit direct or indirect activation of proteolytic clotting factors, are sufficiently known by a person skilled in the art and comprise for example phospholipids, for instance negatively charged phospholipids; lipoproteins, for instance thromboplastin; proteins, for instance tissue factor, activated serine proteases, for instance factor IIa (thrombin), factor VIIa, factor IXa, factor Xa, factor XIa, factor XIIa or activated protein C; snake venoms, for instance PROTAC® enzyme, ecarin, textarin, noscarin, batroxobin, thrombocytin or Russell's viper venom (RVV); contact activators, for instance silica, kaolin, ellagic acid or Celite. Other substances that can contain an agent are e.g. buffer substances, salts, detergents, ions, especially calcium ions and chelating agents.

In an embodiment of the method for determining the activity of a proteolytic clotting factor, the sample is additionally mixed with a fibrin aggregation inhibitor. Fibrin aggregation inhibitors are substances that prevent the aggregation of thrombin-induced fibrin monomers. In this way, the formation of a fibrin clot in a fibrinogen-containing sample is prevented, which might otherwise have an adverse effect on measurement, for example by limiting diffusion and quenching. Preferred fibrin aggregation inhibitors are synthetic peptides, for instance a peptide of the sequence glycine-proline-arginine-proline (commercially available as Pefabloc® FG, Pentapharm, Switzerland). Other preferred peptides that can be used as fibrin aggregation inhibitors, in particular the preferred peptide of the sequence glycine-proline-arginine-proline-alanine, are described in EP-A2-456152.

Once the reaction mixture, which contains the sample, a substrate that can be bound and modified by the enzyme to be determined, and a first and second component of a signal-forming system, has been prepared, the reaction mixture is incubated for a limited time, to ensure sufficient association of enzyme and substrate. The term "sufficient" means that the method as a whole makes quantitative determination of the activity of the enzyme possible. The optimum incubation time of a particular assay system can be determined experimentally. The signal or the variation of the signal over time, which is produced in the reaction mixture, is correlated with the activity of the enzyme to be detected or with an activity modulator. Based on this correlation, the activity of an enzyme can be determined from the signal or the temporal variation of the signal. For this, calibration with a standard is preferably carried out. The standard has a defined activity or concentration of the enzyme or of the activity modulator.

According to further embodiments a homogeneous method can be provided, which apart from specific determination of the enzyme activity, makes possible the simultaneous determination of the amount of enzyme in the same reaction mixture.

According to further embodiments, a third component of the signal-forming system is also added to the sample being investigated, and this becomes associated with the enzyme to be determined during incubation. The third component of the signal-forming system is such that a second detectable signal is produced, which is different from the first signal and is only produced if the third and the second component of the signal-forming system are brought spatially close to one another by simultaneous binding to the enzyme to be determined. The second signal produced is proportional to the amount of enzyme in the sample.

This method for simultaneous determination of the activity and amount of an enzyme in one and the same reaction mixture has the advantage that it is possible to establish in a single test run whether the cause, e.g. of lower enzyme activity than the norm, is a reduced amount of enzyme or whether the amount of enzyme corresponds to the norm and therefore another cause has to be assumed for the reduced enzyme activity, for instance the presence of an activity modulator, such as an inhibitor, or a functional disturbance of the enzyme. The simultaneous determination of various parameters in a single reaction mixture has in addition the advantage that possible inaccuracies in the pipetting of the sample or inaccuracies that could be caused by an aging process of the sample are avoided. Therefore accurate determination of the specific enzyme activity is possible.

The third component of the signal-forming system is such that a second detectable signal is produced, which is different from the first signal and is only produced if the third and the second component of the signal-forming system are brought spatially close to one another by simultaneous binding to the enzyme to be determined. The third component of the signal-forming system can be either an alternative energy donor or an alternative energy acceptor. The third component of the signal-forming system can also be associated with a particulate solid phase.

In one embodiment of the simultaneous determination of the amount of enzyme, the enzyme to be determined additionally has a first binding partner C of a third binding pair C/D, wherein the second binding partner D of the third binding pair C/D is associated with the third component of the signal-forming system and wherein the enzyme is bound to the third component of the signal-forming system through binding of the binding partners C and D during incubation. The third binding pair C/D must be different from the second binding pair X/Y.

The binding partners C and D are two different molecules, which recognize and bind one another specifically. C is an enzyme-specific structural or sequence epitope and D is depending on the nature of the enzyme to be detected—an antibody or antibody fragment or a polynucleotide with specificity for the enzyme-specific structural or sequence epitope.

In one embodiment, for example the first component of the signal-forming system is a first chemiluminescent agent, the second component of the signal-forming system is a photosensitizer, and the third component is a second chemiluminescent agent, wherein the first and second chemiluminescent agents have emission spectra different from one another. Measurement of the two light signals with different emission spectra makes possible on the one hand the quantitative determination of enzyme activity and the quantitative determination of the amount of enzyme in the same reaction mixture.

In another embodiment, for example the first component of the signal-forming system is a first photosensitizer, the second component of the signal-forming system is a chemiluminescent agent and the third component is a second photosensitizer, wherein the first and second photosensitizers are excitable by light of different wavelength. Measurement of the light signal after excitation of the first photosensitizer with light of a wavelength X makes quantitative determination of the enzyme activity possible. Measurement of the light signal after excitation of the second photosensitizer with light of a wavelength Y makes possible the quantitative determination of the amount of enzyme in the same reaction mixture.

According to yet further embodiments, a homogeneous method can be provided, which makes it possible to determine a modulator of enzyme activity.

A "modulator of enzyme activity" means a substance which, as inhibitor, activator, agonist, antagonist or cofactor, is able to influence (modulate) the activity of an enzyme.

According to further embodiments, a defined amount of an enzyme, whose activity can be influenced directly or indirectly by the modulator of enzyme activity to be determined, is added in the form of a separate reagent to the sample being investigated. In addition, a substrate that can be bound and modified by the added enzyme, and a first and a second component of a signal-forming system, wherein the first component of the signal-forming system is or will become associated with the substrate and wherein the second component of the signal-forming system is associated with the added enzyme, are added to the reaction mixture. The signal-forming system is such that a detectable signal is only produced if the first and the second component of the signal-forming system are brought spatially close to one another by binding of the enzyme to be determined to the substrate. The measured signal is correlated with the enzyme modulating activity of the enzyme modulator in the sample.

The method according to various embodiments is suitable both for determining enzyme inhibitors and for determining enzyme activators. For determining an enzyme inhibitor, the enzyme is added in activated form to the reaction mixture. For determining an enzyme activator, the enzyme is added in non-activated form to the reaction mixture.

In particular, the method according to various embodiments is suitable for the determination of anticoagulants, i.e. substances that inhibit the activity of certain blood clotting factors.

For the determination of an anticoagulant in a sample, a known, defined amount of an activated clotting factor is added to the reaction mixture. Which activated clotting factor is added depends on which anticoagulant is to be determined.

For determination of a heparin, i.e. a high-molecular, unfractionated heparin (HMW heparin) or a low-molecular heparin (LMW heparin) or a heparinoid, in particular addition of factor IIa (thrombin) or of factor Xa is suitable. For determination of a direct thrombin inhibitor, e.g. argatroban, melagatran, ximelagatran, bivalirudin, dabigatran or hirudin, in particular addition of factor IIa (thrombin) is suitable. For determination of a direct factor Xa inhibitor, e.g. rivaroxaban, in particular addition of factor Xa is suitable.

Regardless of the fact that in the method according to various embodiments for quantitative determination of an enzyme modulator, a defined amount of an enzyme, whose activity can be influenced directly or indirectly by the enzyme modulator to be determined, and wherein the enzyme is contained in a separate reagent, which is added to the reaction mixture, the above explanations for carrying out the method of determining the activity of an enzyme also apply to the method according to various embodiments for quantitative determination of an enzyme modulator.

The enzymatic reaction can be measured over the entire time interval of the reaction until establishment of equilibrium or in at least one specified time interval or at least one point of time. For determining the activity, the measured values can be used per se or with reference to a time interval. If the activity is determined from photometric data relating to a time interval, i.e. the conversion or reaction rate is detected, various methods can be used for determining the conversion or reaction rate. For example, the conversion rate can be determined by means of time-conversion curves. For time-conversion curves, the reaction of the substrate is plotted against time. For determining the conversion rate, a straight line is constructed in the region of the zero-order reaction of the time-conversion curve, usually at the start of measurement of an enzyme reaction. The slope of the straight line then gives the conversion rate, i.e. the change in concentration of the substrate or product in a specified time interval.

Measured quantities or parameters that are suitable for evaluating the kinetics of conversion are for example all parameters that describe the reaction kinetics, for instance the discussion of curves per se, but especially individual parameters of the reaction kinetics, such as the maximum slope, i.e. the reaction rate ($v_{max}$), sigmoidicity parameter, linearity parameter, the area under the curve, etc. Parameters that are suitable for test evaluation are e.g. also absolute measured values, for instance LOCI measured values, which are measured at a specified point of time, or a point of time at which a specified measured value, e.g. a maximum value, is reached.

In the conversion of a substrate, enzymes react with their substrates under suitable conditions and form an enzyme-substrate complex. If the conditions are selected appropriately, in a further step there may be conversion of the substrate to at least one product.

Through the use of a "signal-forming system", various temporal relations of the signal can be utilized for determining enzyme activities.

When the binding partner of the signal-forming system for the enzyme is used at sufficient concentration, the concentration and thus the activity of the free enzyme (FE) can be neglected, if the system is at equilibrium. Otherwise, at least at the start of the reaction, the formation of the complex of enzyme and binding partner of the enzyme can affect the signal. Enzyme bound to the binding partner (BE) can react with the substrate. For the substrate, a distinction has to be made between free substrate (FS) and substrate bound to the corresponding binding partner of the signal-forming system (BS). BE accordingly binds either FS or BS, i.e. S and FS compete with each other for binding to the BE. The same applies correspondingly to the conversion of FS or BS. It has to be borne in mind that FS and BS need not necessarily have the same affinity for BE. Binding of a substrate to the signal-forming system can lead to a change in affinity. If the affinity of FS is higher than that of BS, more FS is bound by BE and vice versa. This also applies to the conversion of FS and BS to a product. The reactivity or convertibility of a substrate to a product may change, i.e. increase or decrease, with binding to the signal-forming system. It is conceivable that the reaction of conversion of a substrate after binding of the substrate to the signal-forming system will be lowered so that the reaction of conversion of the bound substrate can be neglected relative to the binding reaction or so that the substrate in the bound form is barely or no longer converted.

When using LOCI as signal-forming system, only binding of BS to BE supplies a signal, therefore competition of FS and BS affects the signal or its kinetics. Said competition depends on the respective concentration, affinity or convertibility of FS and BS.

If the amount of substrate is selected so that there is mainly BS, the concentration of FS can be neglected. FS then plays hardly any role in signal formation. That is, the concentration, affinity and convertibility of BS then have a decisive influence on the signal or its kinetics. If the reaction of conversion of BS is dominant over the binding reaction, a decrease of the signal with time is to be expected. Conversely, if the binding reaction predominates over the reaction of conversion, at first an increase of the signal with time is to be expected. This situation is represented in example 1. If there is a sufficient reaction of conversion, at a later point of time there may again be a decrease of the signal with time, when binding approaches the equilibrium state.

The following examples serve to illustrate the present invention and are not to be understood as any limitation.

EXAMPLES

Materials

Unless stated otherwise, all reagents are from Sigma-Aldrich Corp. (St. Louis, Mo., USA).

Substrates

The following FSAP-sensitive peptides were prepared by the standard Fmoc peptide synthesis procedure:
1. a pentapeptide, coupled to biotin with the amino acid residues arginine, proline, arginine, phenylalanine, lysine in the stated sequence and with a biotin on the C-terminal lysine residue (peptide I);
2. a tetrapeptide, coupled to biotin with the amino acid residues isoleucine, proline, arginine, lysine in the stated sequence and with a biotin on the C-terminal lysine residue (peptide II);
3. a peptide according to 1 or 2 with a polyethylene glycol with 12 ethylene glycol units ($PEG_{12}$ spacer) between the N-terminal lysine residue and the biotin (peptides III according to 1 and peptide IV according to 2).

Signal-Forming System

The signal-forming system used here is based on the known LOCI technology (luminescent oxygen channeling assay, see also EP-A2-0515194). The system comprises a photosensitizer and a chemiluminescent agent. Excitation of the photosensitizer with light causes the production of short-lived singlet oxygen, which is able to activate the chemiluminescent agent, so that a luminescence signal is emitted.

Chemibeads

The first component of the signal-forming system is designated as Chemibead hereinafter. It comprises the chemiluminescent agent, which is associated with a particulate latex solid phase. Chemibeads were conjugated with a monoclonal anti-FSAP antibody (Siemens Healthcare Diagnostics Products GmbH, MAk No. 1102-677(26)), which is formed from the hybridoma cell line DSM ACC2453 (see EP-A1-1650305), by the following procedure: The antibody was buffered in a Sephadex® G-25 column in 300 mM NaCl, 0.05% Tween® 20, 10 mM phosphate buffer, pH 7.0 and concentrated to 20 mg/mL. 4 mg of antibody was coupled covalently to 20 mg Chemibeads with addition of 25 mg/mL NaCNBH3. After an incubation step and blocking of reactants that are still free, the antibody-conjugated Chemibeads were purified by diafiltration and then taken up in 50 mM HEPES, 300 mM NaCl, 1 mM EDTA, 0.1% Triton® X-405, 1 mg/mL BSA, 0.15% PROCLIN® 300, 0.1 mg/mL neomycin sulfate, pH 8.0.

Sensibeads

The second component of the signal-forming system is designated as Sensibead hereinafter. It comprises the photosensitizer (trihexyl) silicone-t-butylphthalocyanine, which is associated with a particulate latex solid phase, which is then streptavidin-coated.

Factor VII Activating Protease (FSAP)

Two-chain FSAP (tc-FSAP) was prepared, as described by Kannemeier et al. (Kannemeier, C. et al. (2001) Factor VII and single-chain plasminogen activator-activating protease: activation and autoactivation of the proenzyme. Eur. J. Biochem. 268 (13): 3789-3796).

Example 1

Method for Determining FSAP Activity

The FSAP-sensitive peptides I-IV described above were dissolved in distilled water at a concentration of 2 mg/mL (concentrate) and for the test were diluted to approx. 20 μg/mL in test buffer (25 mM HEPES, 140 mM NaCl, 10 mM CaCl$_2$, 1% Tween® 20, 1% BSA and 1% dextran T-500, pH 6.3). The Chemibeads were diluted to 200 μg/mL and the Sensibeads to 400 μg/mL in test buffer.

Assay I:

120 μL of test buffer were mixed with 10 μL of anti-FSAP Chemibeads, 10 μL of purified tc-FSAP in test buffer (10 μg/mL), 10 μL biotinylated peptide substrate and 10 μL Sensibeads and incubated in DIMENSION VISTA® reaction cuvettes (Siemens Healthcare Diagnostics Products GmbH, Marburg, Germany) for 10 minutes at 37° C. This was followed by kinetic measurement of the chemiluminescence of the reaction mixture, also called LOCI® signal hereinafter, for 30 minutes in a commercially available DIMENSION VISTA® LOCI® measuring unit (Siemens Healthcare Diagnostics Products GmbH). For each measurement point, the reaction mixture was illuminated for 200 ms with light at a wavelength of 680 nm and the resultant LOCI® signal was measured for 1000 ms at 612 nm.

In one test series, signal formation was investigated when using the four peptide substrates I-IV described above. Table shows the signal formation in kilocounts (kcounts) of the four peptide substrates investigated in the presence of the active enzyme and without enzyme. All four biotinylated peptides investigated only showed a definite signal dynamics for 30 minutes in the presence of the active enzyme. If no enzyme is present, no significant variation of the signal with time can be detected.

TABLE 1

| | Measurement kinetics [min.] | Peptide I [kcounts] | Peptide II [kcounts] | Peptide III [kcounts] | Peptide IV [kcounts] |
|---|---|---|---|---|---|
| Assay | | | | | |
| Assay I (all components) | 2 | 25.013 | 23.352 | 18.237 | 17.364 |
| | 5 | 37.83 | 35.704 | 29.534 | 26.484 |
| | 10 | 59.635 | 54.607 | 49.056 | 45.347 |
| | 15 | 85.131 | 79.409 | 72.159 | 66.918 |
| | 30 | 144.879 | 128.201 | 88.234 | 81.497 |
| Negative control | | | | | |
| Assay I (without tc-FSAP) | 2 | 15.456 | 13.875 | 1.946 | 2.877 |
| | 5 | 16.814 | 14.672 | 2.231 | 3.214 |
| | 10 | 16.478 | 16.427 | 2.433 | 3.544 |
| | 15 | 17.127 | 16.127 | 2.412 | 3.724 |
| | 30 | 16.972 | 16.423 | 2.573 | 3.709 |

As well as simple detection of an active enzyme, it can also be determined quantitatively. Table 2 shows the dependence of the LOCI signal on the concentration of active FSAP (two-chain (tc) form). For determining FSAP activity, a tc-FSAP dilution series was tested in test buffer (18 to 600 plasma equivalent units (PEU)/mL or 1.5 to 50 μg/mL) at a peptide substrate concentration of 20 μg/mL, as described in assay I. Measurements were taken after incubation for 30 minutes at 37° C. Table 2 shows that the concentration and the associated activity of the FSAP are correlated with the signal and therefore can also be quantified. Quantification can for example be carried out by calibration with a corresponding standard of active FSAP with known activity. If no tc-FSAP or no peptide substrate is added in the assay, there is no signal formation (Table 3).

TABLE 2

| tc-FSAP [μg/mL] | tc-FSAP [PEU/mL] | Signal [kcounts] |
|---|---|---|
| 0 | 0 | 2.735 |
| 1.5 | 18 | 51.4 |
| 3 | 36 | 80.146 |
| 6 | 72 | 101.731 |
| 12.5 | 150 | 116.522 |
| 25 | 300 | 146.279 |
| 50 | 600 | 215.144 |

TABLE 3

| tc-FSAP [μg/mL] | Peptide substrate [μg/mL] | Signal [kcounts] |
|---|---|---|
| 12.5 | 0 | 2.391 |
| 0 | 20 | 2.735 |
| 12.5 | 20 | 116.522 |

FIG. 1 shows the dependence of the LOCI signal on the enzyme activity or concentration, based on the data from Table 2. The two-phase dependence is interesting. A sharp increase in signal is seen at low FSAP concentrations. It is less pronounced at higher concentrations. It can be assumed that in the low concentration region the increase in enzyme concentration and therefore the proportion of bound enzyme contribute to signal formation to a greater extent than at higher concentrations. Conversely, in the higher range of enzyme concentration, the binding reaction or reaction of conversion contributes to the signal or to the change in signal to a greater extent.

The antigen concentration of an enzyme need not necessarily correlate with the activity of the enzyme. For example, as the FSAP circulates in the plasma both as inactive zymogen (single-chain (sc) form) and as active enzyme (tc-FSAP), a one hundred percent correlation between the FSAP-antigen concentration and the FSAP is not necessarily ensured. With the method according to various embodiments, both the activity and the amount of the enzyme can be determined. Therefore the specific activity of an enzyme can also be detected.

Figure 2:
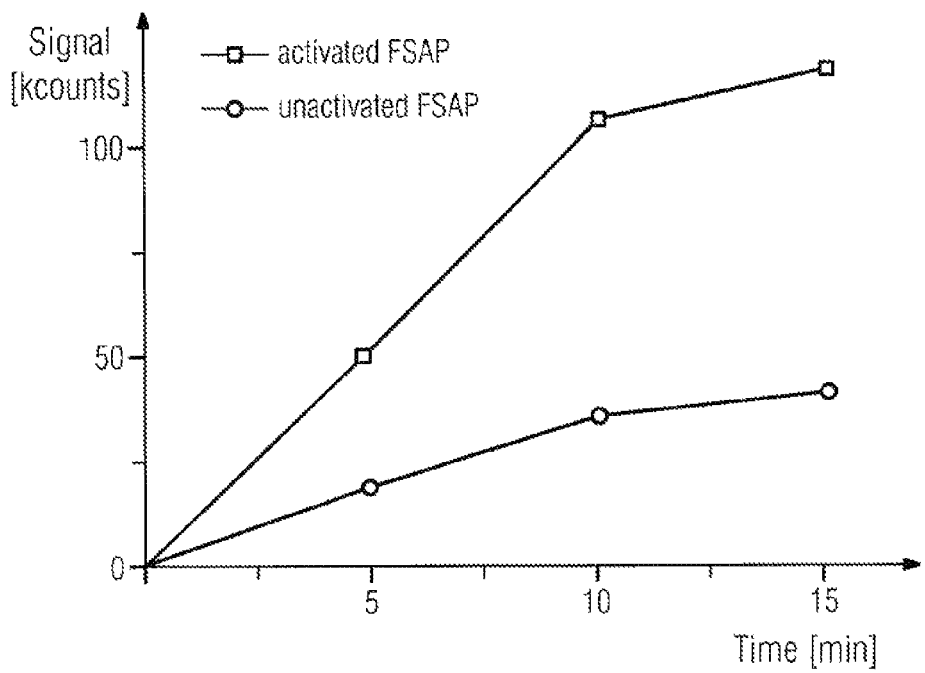
FIG. 2 shows the influence of dextran sulfate (DXS) as cofactor of activation of FSAP in plasma.

In order to clarify this, to activate the sc-FSAP, citrate plasma was preincubated for 15 minutes in test buffer with 20 μg/mL of high-molecular dextran sulfate (dextran sulfate sodium salt from Leuconostoc spp., average molecular weight 500 kDa) and was tested in comparison with a sample without addition of high-molecular dextran sulfate for activation of the FSAP. Activation in the presence of dextran sulfate leads to a different signal height and signal dynamics versus the same sample, with the same FSAP concentration, but without activation by dextran sulfate (Table 4 and FIG. 2). The signal height produced by activation of the FSAP roughly corresponds to the signal of a purified tc-FSAP of equal concentration of 12 μg/mL with an enzyme activity of 1 PEU/mL (not shown).

TABLE 4

Influence of dextran sulfate (DXS) as cofactor of activation of FSAP in plasma

| | Test buffer with DXS (20 µg/mL, MW ≥ 500 kDa) Peptide concentration [µg/mL] | | Test buffer without DXS Peptide concentration [µg/mL] | |
|---|---|---|---|---|
| Incubation time at +37° C. | 10 signal [kcounts] | 0 signal [kcounts] | 10 signal [kcounts] | 0 signal [kcounts] |
| 5 | 50.303 | 1.166 | 19.359 | 0.856 |
| 10 | 106.500 | 1.220 | 36.009 | 1.005 |
| 15 | 118.096 | 1.204 | 41.630 | 0.823 |

As noted previously, it can be assumed that the influence of enzyme activity on signal formation in comparison with enzyme concentration increases with increasing reaction time. This is clear from FIG. 2.

The ratio of the signals at 15 minutes to 5 minutes incubation is approx. 2.35 for the activated FSAP, and approx. 2.15 for the unactivated FSAP. If it is assumed that at a later point of time the enzyme activity makes a larger contribution to signal formation than the enzyme or antigen concentration, the higher signal ratio of 2.35 versus 2.15 is an indicator of a higher specific activity of the FSAP in the activated sample versus the unactivated sample.

The situation is similar with the ratio of the signals of activated FSAP to unactivated FSAP at 15 and 5 minutes, of 2.84 and 2.6. The higher signal ratio is once again a measure of the higher specific activity of the FSAP in the activated sample versus the unactivated sample.

Other parameters of the time dependence of the signal can also be used as a measure of the antigen or enzyme concentration and the enzyme activity and the resultant specific activity. For example, for the activated FSAP the slope gives a value of 10.65 kcounts/min up to 10 minutes, and 2.32 kcounts/min after 10 minutes.

The slope for the unactivated FSAP up to 10 minutes gives a value of 3.60 kcounts/min and after 10 minutes, 1.12 kcounts/min.

The reduction in signal increase with time (slope) after 10 minutes is markedly higher for the activated FSAP than for the unactivated FSAP. The reduction can for example be quantified by the ratio or the difference of the slopes, i.e. approx. 3 versus 2 and 7 versus 1.2. The higher conversion of the bound substrate by the more active FSAP, in comparison with the more inactive FSAP presumably leads to a markedly reduced increase in signal with time. In principle, other parameters of a discussion of curves can also be employed for determining antigen concentration, enzyme activity or specific activity.

Example 2

Method for Determining an Inhibitor of an Enzyme Activity

Determination of the specific activity of an enzyme can also provide information about the possible presence of activity modulators. However, the method according to various embodiments also permits quantification of the influence and therefore also quantitative determination of activity modulators. This is shown in the following for the example of an inhibitor of FSAP, aprotinin. The signal or its course varies as a function of the concentration of the inhibitor.

The kinetics of enzyme-inhibitor interaction was investigated by measuring enzyme activity as a function of the amount of inhibitor. In the tc-FSAP inhibition assays, constant amounts of enzyme (tc-FSAP, µg/mL) were preincubated with variable inhibitor concentrations (aprotinin from bovine lung, Fluka), to enable formation of the enzyme-inhibitor complex. Another assay was carried out without preincubation. The remaining protease activity was determined after adding the peptide substrate, as described in example 1.

Assay System:

120 µL test buffer pH 6.3, 10 µL anti-FSAP Chemibeads (200 µg/mL in test buffer), 10 µL purified tc-FSAP (10 µg/mL) and 10 µL test buffer with 0, 4.7 and 47.2 U/mL aprotinin were mixed in DIMENSION VISTA® LOCI® reaction cuvettes. Addition of 10 µL of biotinylated peptide substrate IV in test buffer and 10 µL Sensibeads (400 µg/mL in test buffer) took place without preincubation or after 10 minutes of preincubation at 37° C. The resultant LOCI® signal was measured kinetically, over a period of 15 minutes at 37° C., in a commercially available DIMENSION VISTA® LOCI® measuring unit (Siemens Healthcare Diagnostics Products GmbH) with 200 ms illumination at 680 nm and 1000 ms measuring time at 612 nm. Aprotinin shows a strong signal-reducing effect, mainly after preincubation with tc-FSAP (Table 5).

TABLE 5

Inhibition of tc-FSAP activity with aprotinin without and with preincubation; measured value after 15 minutes

| Aprotinin [U/mL] | Without preincubation Signal [kcounts] | With 10 min preincubation Signal [kcounts] |
|---|---|---|
| 0 | 117.27 | 117.27 |
| 4.7 | 71.18 | 15.03 |
| 47.3 | 67.8 | 11.77 |

Another inhibitor used was a monoclonal antibody that inhibits FSAP activity (Siemens Healthcare Diagnostics Products GmbH, MAk No. 1102/570), which is directed against the light chain of FSAP and is formed by the hybridoma cell line DSM ACC2533 (see EP-A2-1334983), similarly to the assay with aprotinin. Table 7 shows the increasing inhibitory effect with increasing concentration of the monoclonal antibody used.

TABLE 7

Inhibition of tc-FSAP activity with anti-FSAP MAk 1102/570

| Anti-FSAP MAk 1102/570 [µg/mL] | Without preincubation Signal [kcounts] |
|---|---|
| 0 | 86.5 |
| 24 | 10.3 |
| 240 | 2.7 |

Both with aprotinin and with the inhibitory antibody, the signal varies with the respective concentration of the activity modulator. With appropriate calibration, this permits quantification of the activity modulator. The inhibitor influences the binding or the conversion of a substrate; of the bound substrate or of the unbound substrate. If the binding or the binding process of the bound enzyme to the bound substrate predominates in the selected assay system, with increasing inhibitor concentration there is a decrease in the absolute signal or a reduction of the increase with time, as shown in the example. Conversely, if the reaction of conversion predominates, there may be an increase in the signal or a decrease in reduction of the signal with time with increasing inhibitor concentration.

Figure 3:
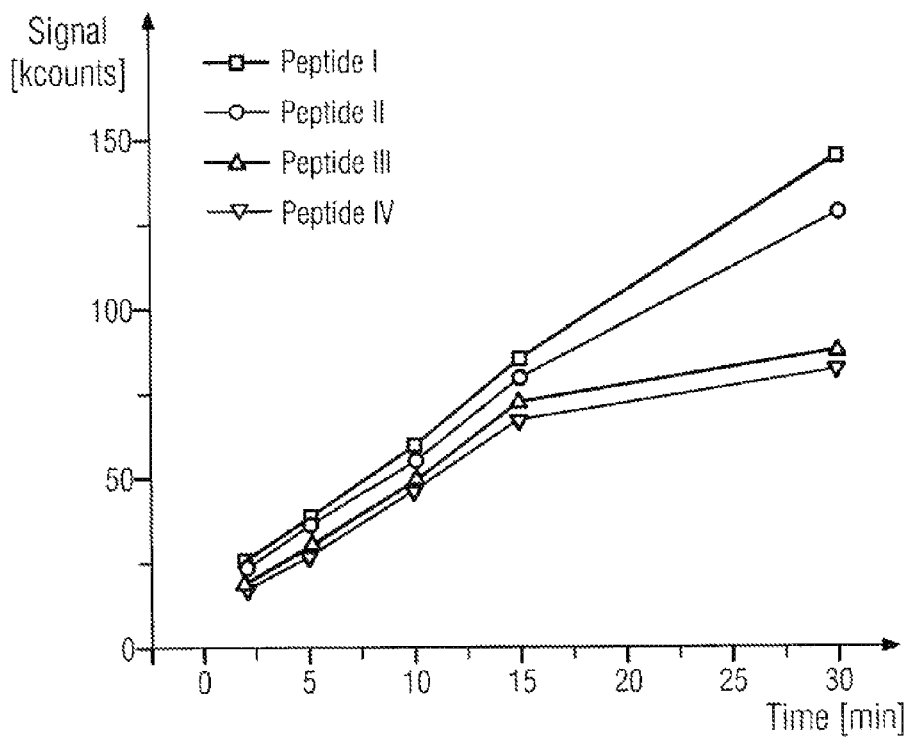
FIG. 3 shows the dependency of signals or the signal dynamics on the type of substrates.

Moreover, the method according to various embodiments permits determination of the properties of substrates. This will be clear from FIG. 3. The signals or the signal dynamics also depend on the type of substrates.

This can possibly be attributed to a different binding reaction and/or reaction of conversion. The increase in signal up to 15 minutes is comparable for the four different peptides. This may indicate that the binding kinetics is comparable. After incubation for 30 minutes, however, the signals compared with peptide I from peptide II and in particular peptides III and IV are much lower. As comparable peptide concentrations were used, this possibly points to different affinities or a difference in conversion of the peptides. For example, the reaction of peptide I bound to the Sensibeads may be greatly restricted by the binding to the Sensibeads. Therefore in particular the signal from formation of the complex of bound enzyme and bound substrate is determined. The conversion of the bound substrate is in this case reduced or is not possible. If, however, the bound substrate is converted, the signal can then no longer increase so strongly, because now there is increase in the proportion of bound product, which is bound less or no longer by the enzyme. Therefore the LOCI signal is reduced. It can therefore be assumed that in particular the bound peptides III and IV are converted better than peptides I and II. It is conceivable that substrates, after they have bound to the Sensibead, can no longer be bound or even converted by the enzyme. Substrates bound to the Sensibead, which are no longer bound by the enzyme, are unsuitable. Bound substrates, which are barely still or no longer measurably converted, but bind enzyme, are still suitable.

Figure 4:
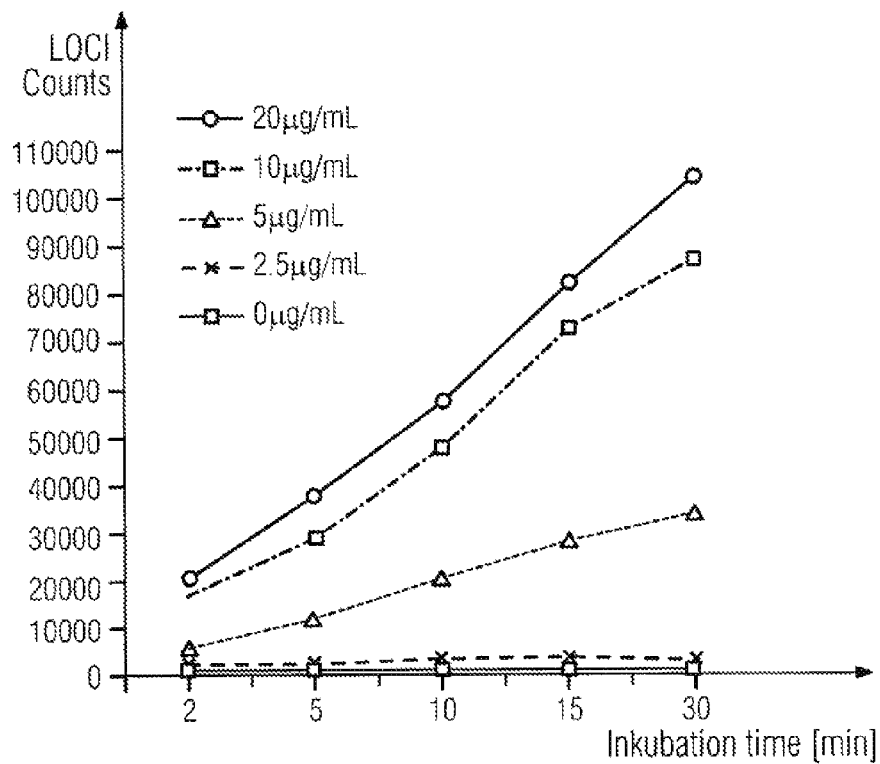
FIG. 4 shows the kinetics of the LOCI signal as a function of the peptide concentration used.

Along with determination of the activity and concentration of an enzyme and differences in behavior with different substrates, another example will demonstrate that the concentration of substrates can also be determined. FIG. 4 shows the kinetics of the LOCI signal as a function of the peptide concentration used. The slope of the signal kinetics increases with increasing peptide concentration.

What is claimed is:

1. A method of quantitative determination of an enzyme modulator in a sample, wherein the method comprises the following steps:
   a) preparing and incubating a reaction mixture containing:
      (i) the sample including an unknown amount of the enzyme modulator,
      (ii) a known amount of an enzyme, whose activity can be influenced directly or indirectly by the modulator of enzyme activity to be determined,
      (iii) a substrate, which can be bound and modified by the enzyme, and
      (iv) a first and a second component of a signal-forming system, where the first component of the signal-forming system is or will become associated with the substrate and where the second component of the signal-forming system is associated with the enzyme, where the signal-forming system is such that a detectable signal is only produced if the first and the second component of the signal-forming system are brought spatially close to one another by binding of the enzyme to the substrate,
   b) measuring the signal, which is correlated with the activity of the enzyme modulator in the sample; and
   c) determining a concentration of the enzyme modulator based on the measured signal.

2. The method according to claim 1, wherein the substrate has a first binding partner A of a first binding pair A/B and wherein the first component of the signal-forming system has a second binding partner B of the first binding pair A/B and wherein the substrate is bound by binding of the binding partners A and B to the first component of the signal-forming system or becomes bound during incubation.

3. The method according to claim 2, wherein the binding partners A and B are selected so that they form the first binding pair A/B from the group comprising FLAG-tag/anti-FLAG-tag antibodies, HIS-tag/anti-HIS-tag antibodies, fluorescein/anti-fluorescein antibodies, biotin/avidin and biotin/streptavidin.

4. The method according to claim 1, wherein the enzyme has a first binding partner X of a second binding pair X/Y and wherein a second binding partner Y of the second binding pair X/Y is associated with the second component of the signal-forming system and wherein the enzyme is bound by binding of the binding partners X and Y during incubation to the second component of the signal-forming system.

5. The method according to claim 4, wherein the binding partners X and Y are selected so that X is an enzyme-specific structural or sequence epitope and Y is an antibody or antibody fragment with specificity for the enzyme-specific structural or sequence epitope.

6. The method according to claim 1, wherein the first component of the signal-forming system is associated with a first particulate solid phase and the second component of the signal-forming system is associated with a second particulate solid phase.

7. The method according to claim 1, wherein the first component of the signal-forming system is a chemiluminescent agent and the second component of the signal-forming system is a photo sensitizer, or vice versa.

8. The method according to claim 1, wherein the enzyme is a peptidase enzyme selected from the group consisting of serine proteases, glycosidases, glycosylases and nucleases.

9. The method according to claim 1, wherein the enzyme is a serine protease enzyme.

10. The method according to claim 1, wherein the enzyme is a proteolytic clotting factor from the group comprising factor II, factor VII, factor IX, factor X, factor XI, factor XII and protein C, wherein additionally an agent for direct or indirect activation of the proteolytic clotting factor in the sample is added to the reaction mixture.

11. The method according to claim 10, wherein the agent is selected from the group comprising thromboplastin, factor IIa, factor VIIa, factor IXa, factor Xa, factor XIa, factor XIIa, activated protein C, snake venoms, negatively charged phospholipids, calcium ions, tissue factor, silica, kaolin, ellagic acid, and Celite.

12. The method according to claim 1, wherein the enzyme is factor VII activating protease (FSAP) and the enzyme modulator modulates the activity of factor VII activating protease.

13. The method according to claim 1, wherein the enzyme is a blood clotting factor and the enzyme modulator is an inhibitor of the blood clotting factor.

14. The method according to claim 13, wherein the inhibitor of the blood clotting factor is selected from the group consisting of heparin, argatroban, melagatran, ximelagatran, bivalirudin, dabigatran, rivaroxaban and hirudin.

* * * * *